United States Patent [19]

Mächler et al.

[11] Patent Number: 4,598,715

[45] Date of Patent: Jul. 8, 1986

[54] INSTRUMENT FOR SPECTRAL MEASUREMENT IN THE BLOODSTREAM

[75] Inventors: Meinrad Mächler; Sibylle Mächler, both of Ellwangen; Richard Sachse, Königsbronn, all of Fed. Rep. of Germany

[73] Assignee: Carl-Zeiss-Stiftung, Heidenheim on the Brenz, Fed. Rep. of Germany

[21] Appl. No.: 733,942

[22] Filed: May 14, 1985

Related U.S. Application Data

[63] Continuation of Ser. No. 488,189, Apr. 25, 1983, abandoned.

[30] Foreign Application Priority Data

Apr. 29, 1982 [DE]  Fed. Rep. of Germany ....... 3215879

[51] Int. Cl.$^4$ .............................................. A61B 5/00
[52] U.S. Cl. .................................. 128/634; 350/96.2; 356/41; 356/326
[58] Field of Search ............ 251/149.2; 128/633, 128/634, 664, 665; 350/96.2, 96.23; 356/41, 326, 328

[56] References Cited

U.S. PATENT DOCUMENTS

| | | | |
|---|---|---|---|
| 3,068,742 | 12/1962 | Hicks, Jr. et al. | 356/41 |
| 3,136,310 | 6/1964 | Meltzer | 356/41 |
| 3,580,414 | 5/1971 | Ginsburgh et al. | 251/149.2 |
| 3,754,564 | 8/1973 | Naumburg et al. | 251/149.2 |
| 3,847,483 | 11/1974 | Shaw et al. | 356/41 |
| 3,911,977 | 10/1975 | Berger | 251/149.2 |
| 4,012,147 | 3/1977 | Walrafen | 356/301 |
| 4,050,450 | 9/1977 | Polanyi et al. | 128/634 |
| 4,171,868 | 10/1979 | Hensel et al. | 350/96.23 |
| 4,213,462 | 7/1980 | Sato | 128/634 |
| 4,214,729 | 7/1980 | Narfgren | 251/149.2 |
| 4,247,164 | 1/1981 | Mannschke | 350/96.2 |
| 4,285,596 | 8/1981 | Landa | 356/328 |
| 4,289,295 | 9/1981 | Allread | 251/149.2 |
| 4,295,470 | 10/1981 | Shaw et al. | 128/634 |
| 4,330,209 | 5/1982 | Hashimoto et al. | 356/328 |
| 4,357,105 | 11/1982 | Loretz | 356/41 |
| 4,423,736 | 1/1984 | De Witt et al. | 128/633 |
| 4,445,753 | 5/1984 | Collignon | 350/96.2 |
| 4,453,218 | 6/1984 | Sperinde et al. | 128/634 |
| 4,461,537 | 7/1984 | Raymer, II et al. | 350/96.2 |
| 4,469,398 | 9/1984 | De Baets et al. | 350/96.2 |

Primary Examiner—Kyle L. Howell
Assistant Examiner—Ruth S. Smith
Attorney, Agent, or Firm—Stonebraker, Shepard & Stephens

[57] ABSTRACT

In an instrument for spectral measurement in the bloodstream, the light-guide probe is developed with a diameter of, at most, 0.5 mm. By plug connections with precisely defined positions of the light guides, the light guide probe is connected to an illuminating device having a xenon lamp and to a diode line spectrometer. The diode line spectrometer has an aperture ratio which includes the aperture of the light guide without trimming or vignetting.

3 Claims, 10 Drawing Figures

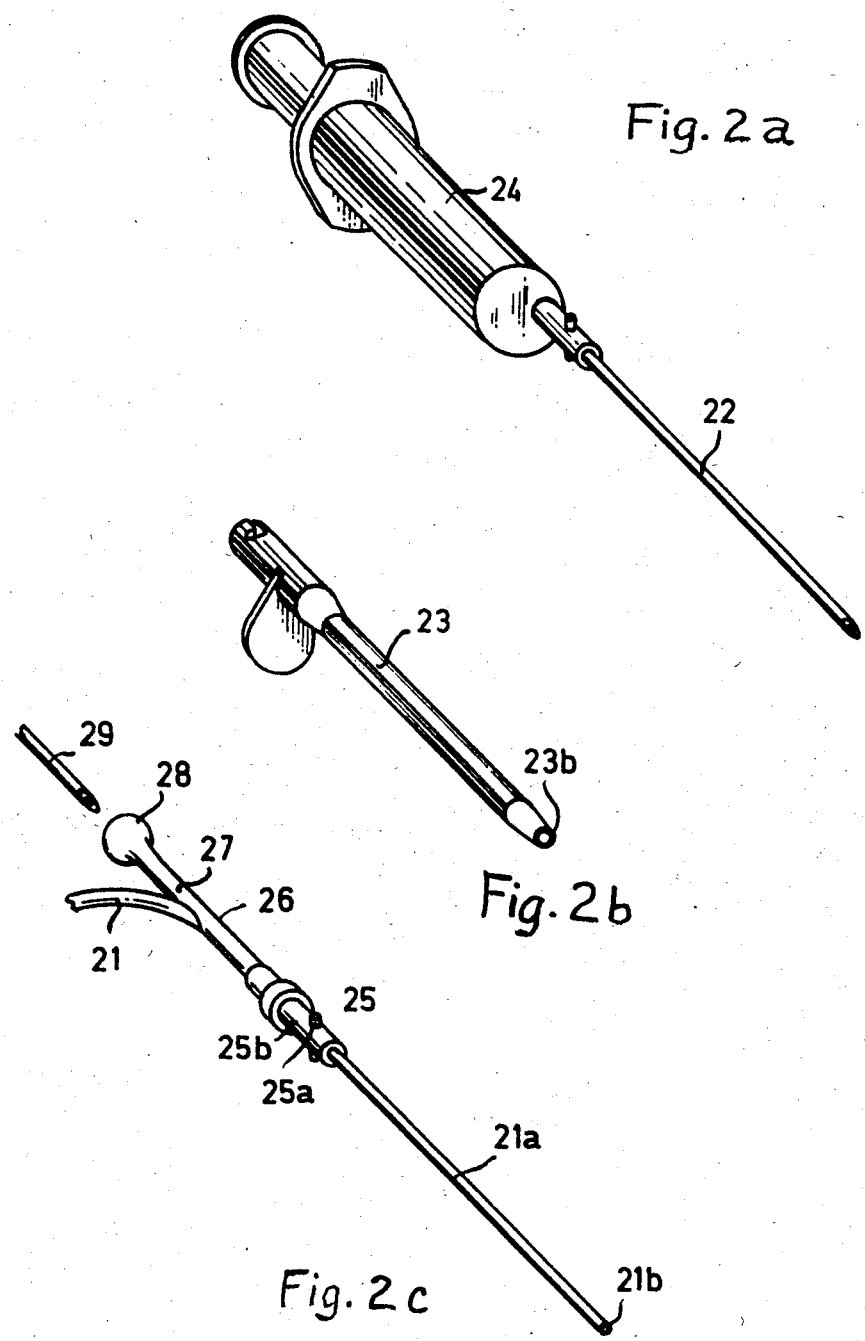

INSTRUMENT FOR SPECTRAL MEASUREMENT IN THE BLOODSTREAM

This is a continuation of application Ser. No. 488,189, filed Apr. 25, 1983 now abandonded.

BACKGROUND OF THE INVENTION

The present invention relates to an instrument for spectral measurement in the bloodstream, having a light-guide probe and a diode line spectrometer.

A photometric measurement in the bloodstream is of importance, for instance, for the continuous measurement of the oxygen content of blood. This is of particular importance for anesthesia since an under-supply of oxygen during anesthesia may lead to severe and irreparable damage to the patient. The only method of measurement which is widely used up to the present time in routine procedure is a polarographic method (the "Oxymeter" of Dräger AG and Hellige GmbH) which has been in use since 1975 and is based on a proposal made by Huck and Lübbers (Arch. Gynäkol. 207, 443, 1969). The method has the disadvantages of an "inflow time" of 15 to 20 minutes, a system-caused delay time of about 15 seconds, the necessity of calibrating before each measurement, and a drift of 10 to 15% within a few hours also inherent in the system. Furthermore, it is necessary to occasionally carry out arterial blood gas analyses for functional verification of the electrode.

From West German unexamined patent application (offenlegungsschrift) No. 27 26 606 there is known a spectral photometer for measurement on tissue surfaces in which the spectrum is made visible on an oscilloscope. The photometer is provided with a photocell array; the measurement head is connected to the apparatus by a light guide.

In unexamined application for a patent of addition (zusatz-offenlegungsschrift) No. 28 15 074 to the aforementioned application, the display screen of the oscilloscope has marks located at the characteristic points of the hemoglobin spectrum to facilitate evaluation.

It is known, for instance from Documenta Geigy, Scientific Tables, 6th Edition, 1960, that the absorption maxima of the spectra of hemoglobin, the reduced form, and of oxyhemoglobin, the oxidized form, shift in characteristic manner: the long-wave absorption maximum shifts from 560 to 577 nm and the short-wave maximum shifts from 430 to 412 nm. The distance between the two maxima therefore changes by 35 nm as a function of the oxygen content, regardless of the absolute value of the absorption. This lack of dependence on the absolute value of the absorption is the most important prerequisite for the possibility of effecting an exact determination of oxygen content. It is known and obvious that the oxygen content "in vivo" can be determined only with the exclusion of atmospheric oxygen. It is furthermore known that the number of erythrocytes, the carrier of the hemoglobin, is about 5 million per cubic millimeter (40 to 45% of the volume of the blood), with an average of 7.5 $\mu$m. This means, that as a result of the high scattering coefficients photometric transmittance measurement would be impossible. On the other hand, however, the opacity is still so great that true reflectance measurement is also not possible.

From an article by Curtis C. Johnson in the Journal of the Association for the Advancement of Medical Instrumentation, 5, 77 (1971), it is known to effect a reflection measurement in vivo with a light-guide measurement head which is introduced into a heart catheter. The measurement is effected with two wavelengths; two LEDs are used as sources of light and a silicon photodiode is used as receiver. The measurement within the heart is necessary due to the large diameter of the light-guide. It is self-evident that such a measurement enters into question only in exceptional cases and is not intended for routine use in normal operations.

From an energy standpoint, the device described by U. Tutschke in Biomedizinische Technik 21, 279 (1976) is much more favorable. An HeNe laser and a pulse dyestuff laser are used for producing the measurement light with two different wavelengths. The much greater luminous intensities than with traditional sources of light result in corresponding return scatter signals so that as compared with other methods it is possible to measure with a more favorable signal-to-noise ratio and/or to use light guides of smaller diameter which make intravasal measurement possible. For routine medical use a measurmeent with two lasers is, however, too expensive, so that such an instrument does not satisfy practical requirements.

The measurement at two wavelengths cannot directly determine the spectral displacement of the absorption maxima but merely the change in intensity of a characteristic wavelength with respect to an isobestic point. For quantitative determinations it is more favorable to have the entire spectral course available in the relevant region and thus improve the accuracy. Furthermore, an instrument which measures the entire course of the specrtrum can be universally used.

The object of the present invention is therefore to provide an instrument suitable for routine medical use which makes it possible to measure the scattered light spectrum of blood within a peripheral vein or artery without interfering with the free circulation of the blood through the blood vessel.

SUMMARY OF THE INVENTION

This object is achieved, in accordance with the present invention, in the manner that the light-guide probe is developed with a diameter of at most 0.5 mm; that the light-guide probe is connected by plug connections, with precisely defined position of the light guides, to a diode line spectrometer and to an illuminating device; and that the diode line spectrometer has an aperture ratio which receives the aperture of the light-guide without trimming.

As a result of the plug connections with precisely defined position of the light guides, the light-guide probe can be replaced without any adjustment or fastening work being necessary and without the operator coming into contact with non-sterile objects. This is an essential advantage for routine operations, since either the light-guide probe must be replaced for sterilization or it must be developed as a sterilized throw-away unit for one-time use.

Due to the large aperture ratio of the spectrometer which receives the aperture of the light guide without trimming, favorable energy conditions are obtained although only a small unit of volume is covered at the place of measurement, since the radiation scattered in a large solid angle is utilized by the small unit of volume.

It is advisable to form the probe of a plurality of light-guide fibers for the conducting of the light to the place of measurement and of a plurality of light-guide fibers for conducting the light away from the place of measurement, and to surround the fibers with inert sleeves in order to protect the fibers from damage and coagulation of the blood.

In one particularly advantageous embodiment, the light-guide fibers are arranged one above the other in the plug connection for the diode line spectrometer, the end surfaces of the light guide fibers forming the entrance slit of the spectrometer.

On the measurement head, the light-guide fibers for the illumination can be arranged concentrically and be surrounded in annular form by the light guide fibers for the measurement. However, it has been found that for measurements in the blood, due to the strong scattering, a mixing together of the light-guide fibers is also favorable insofar as this is effected to some extent statistically.

In one suitable embodiment, the light-guide probe is developed for introduction into an indwelling catheter. It is particularly favorable to provide one or more wash channels in the light-guide probe so that the attachment of blood corpuscles to the measurement head can be prevented.

The use of a xenon lamp as a source of light not only offers an energy advantage but also assures greater reliability in operation, since a xenon lamp cannot be re-ignited after the end of its life but it practically never goes out during operation.

BRIEF DESCRIPTION OF THE DRAWINGS

The invention will be explained in further detail with reference to the drawings in which:

FIG. 2a is a perspective view of a cannula or hollow needle and an attached syringe;

FIG. 2b is a perspective view of an indwelling catheter which may receive either the cannula of FIG. 2a or the light-guide probe of FIG. 2c;

FIG. 2c is a perspective view of a light-guide probe and associated parts;

DESCRIPTION OF THE PREFERRED EMBODIMENTS

Figure 1:
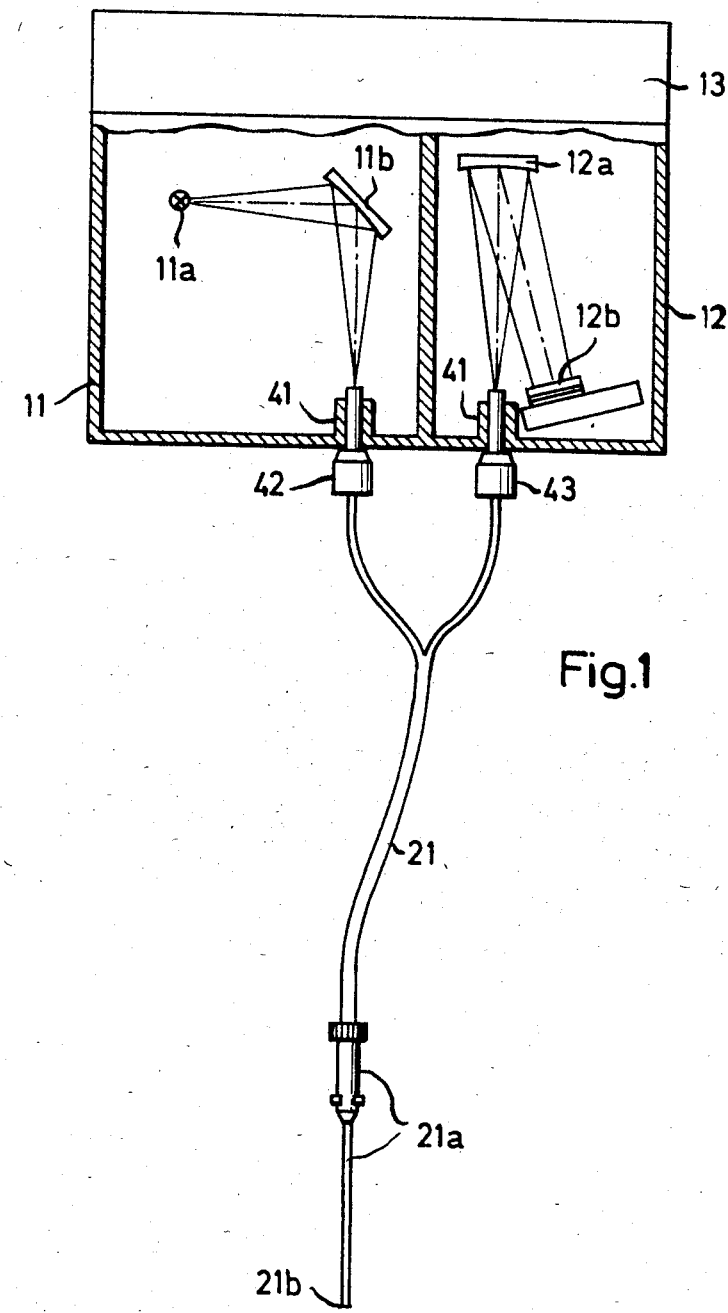
FIG. 1 is a diagrammatic showing of the construction of the new instrument.

Referring to FIG. 1, 11 is an illuminating device, 12 a spectrometer, and 13 the power supply and electronics unit for the illuminating device and spectrometer. The illuminating device 11 has a xenon lamp 11a, an elliptical concave mirror 11b, and a mounting part 41 for the plug connection 42 of the light-guide probe 21. The second plug connection 43 of the light-guide probe 21 is seated in the mounting part 41 of the spectrometer 12, which furthermore contains a concave grating 12a and a diode cell 12b. The measurement head 21a of the light-guide probe 21, shown near the bottom of FIG. 1, is shown on a larger scale in FIG. 2c. It can be introduced into the indwelling catheter 23 (FIG. 2b) instead of the cannula 22 (Fig. 2a), after the catheter, together with the cannula 22 and possibly with the hypodermic syringe 24, has been introduced into a peripheral vein or artery of the patient.

Figure 3:
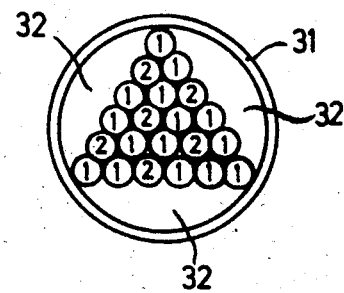
FIG. 3 illustrates an example of the distribution of the light-guide fibers for illumination and measurement on the measurement head.

The measurement head or light-guide probe 21a consists of a thin-walled cannula which surrounds the individual light-guide fibers of which the light guide consists. FIG. 3 is a greatly enlarged end view or schematic cross section through the tip 21b of the measurement head 21a. The light-guide fibers marked 1 come from the illuminating device 11, the light-guide fibers marked 2 go to the spectrometer 12. The individual light-guide fibers are sheathed in known manner by an inert plastic, for instance teflon, which is applied by a polymerization process. This sheathing substantially improves the resistance to breaking of the light-guide fibers, prevents coagulation of the blood, and produces the coherence of the triangular cross section of the light guide, shown by way of example in FIG. 3. The spaces 32 between this triangular cross-section and the cannula wall 31 can be used as conduits for the passage of a wash liquid by which blood corpuscles are prevented from depositing on the tip of the measurement head.

The individual light guides 1 and 2 have a diameter of, for instance, 50 $\mu$m. For the arrangement of the light-guide fibers marked 2 which extend to the spectrometer 12, a statistical distribution within the other light-guide fibers has proven sufficient.

At the end of the measurement head 21a there is seated, as transition to the flexible light guide 21, the fastening part 25 which has an interlock 25a, such as radial pins, and a slightly conical part 25b, which fits tightly in the indwelling catheter 23 when the pins 25a are properly engaged in bayonet slots in the catheter. This makes a reliable and tight attachment possible. The tip 21b of the measurement head terminates flush with the front tip 23b of the catheter. The taper of the conical part 25b is so slight that it is not apparent in the drawing.

Behind the fastening part 25, the outer covering of the light guide has a branching part or section 26 by which the channels 32 shown in FIG. 3 for the wash liquid are branched off into a tube part 27. This tube part connects with a perforatable membrane 28 which can be perforated in known manner by the hypodermic needle 29 for the introduction of the wash liquid.

The division of the light guide 21 into the two branches for the illuminating device 11 and the spectrometer 12 is effected advisedly just in front of those instruments, so that there is practically only one connection between the measurement head 21a and the instruments. In one advantageous embodiment, the light-guide fibers are surrounded by a shrink tube which is shrunk-on, for instance, at the time of the sterilization of the fiber array.

Figure 4A:
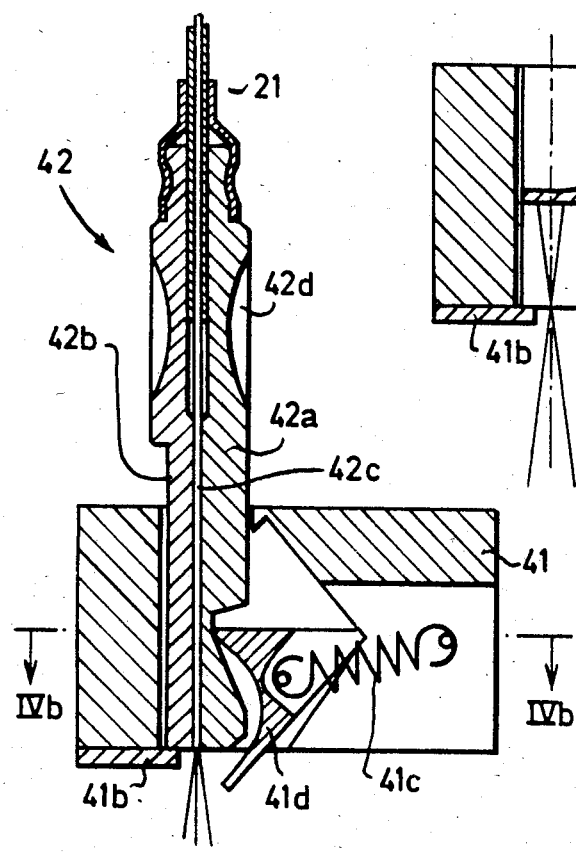
FIGS. 4a, 4b, and 4c show an embodiment of the plug connections.
Figure 4C:
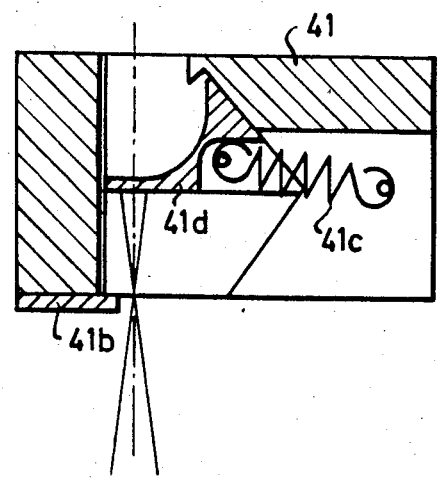
Figure 4B:
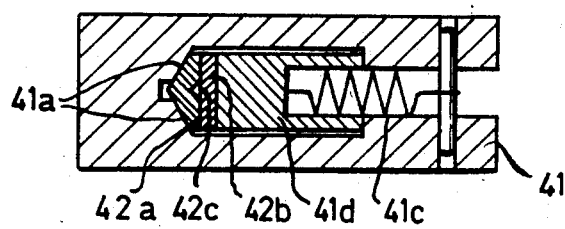

FIGS. 4a, 4b, and 4c show, on a larger scale, some details of the plug connection 42 of the light-guide probe 21 introduced into the mounting part 41. FIG. 4a shows a section in the plane of the optical axis of the light-guide probe 21 and FIG. 4b a section perpendicular thereto, i.e. parallel to the housing wall of the illuminating device 11. The plug connection 42 consists of two parts 42a and 42b. They can be manufactured with great accuracy, for instance, as plastic injection moldings. They are cemented together with the recess 42c between them after the insertion of the light fibers in the recess, or they may be held together in some other manner. The grip troughs 42d facilitate insertion and removal from the mounting part 41. This mounting part constitutes socket means which has a prismatic resting surface or V-shaped portion 41a and a stop 41b against which, after insertion, the part 42b of the plug connection is pressed by the spring 41c and the turnably supported part 41d which constitutes latch means holding the plug in the socket means. In this way the light fibers arranged in the recess 42c always come into a precisely defined position. When the plug connection 42 is pulled out of the mount 41, the rotatably supported part 41d swings into the position shown in FIG. 4c and closes off the illuminating device so that no radiation of the xenon lamp can penetrate toward the outside.

Figure 5A:
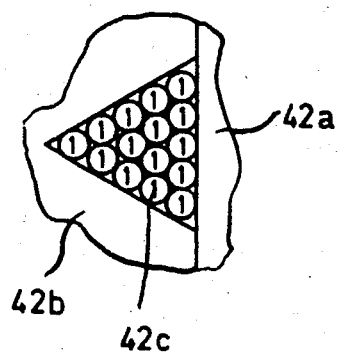
FIGS. 5a and 5b illustrate embodiments for the arrangement of the light guide in the plug connections.
Figure 5B:
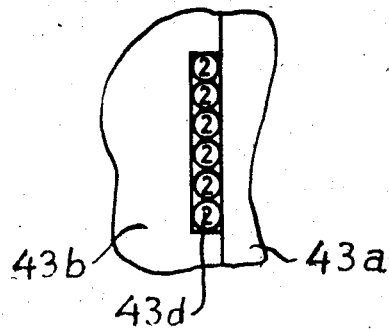

The arrangement of the light-guide fibers on the instrument-side ends of the plug connections 42 and 43 respectively is shown in FIG. 5a for the illuminating device 11 and in FIG. 5b for the spectrometer 12. In the same way as in FIG. 3, the light fibers which go to the illuminating device are marked 1 and the light fibers which go to the spectrometer are marked 2. In FIG. 5a, the part 42b has a triangular recess 42c which is so dimensioned that, for instance, 15 light fibers in very dense packing just fit in it. The light spot of the xenon lamp 11a is focused on the initial surfaces or input ends of these light fibers, as shown in FIGS. 1 and 4a. Due to the triangular arrangement of the light fibers, good utilization of the intensity of radiation of the source of light is obtained in a simple manner. Of course, a four-sided, six-sided or circular arrangement of the light fibers is also possible.

FIG. 5b shows the arrangement of the light fibers 2 in the plug connection to the spectrometer. In this case the grooved or recessed part 43b has a recess 43d which is rectangular rather than triangular, and which is so dimensioned that, for instance, six light fibers 2 just fit therein. The exit end surfaces of these light fibers form the entrance slit of the spectrometer 12.

In addition to the entrance slit formed in this manner, the spectrometer comprises also the holographically produced concave grating 12a and the diode line 12b. Without any further imaging means such as lenses, mirrors or the like, the spectrometer is, on the one hand, completely illuminated directly from the light-fiber ends and, on the other hand, the aperture of the light guide is completely covered. Only with a holographically produced refraction grating is such an arrangement possible, since only with it can the most important imaging errors (astigmatism and spectral curvature) be corrected, provided that the grating is operated with the same geometry as that with which it is holographically produced.

As an example of a suitable dimensioning of the spectrometer, the following data may be indicated: Radius of the spherical concave grating = 2 × focal length 116.3 mm; diameter of the free opening of the circular grating 60 mm; the aperture ratio of the spectrometer is thus 1:1.94 which corresponds to an aperture angle of 30° and thus to the aperture angle of light guides.

The two plug connections 42 and 43 are advisedly so developed that they cannot be interchanged so that the connections to the illuminating device and the spectrometer cannot be improperly made. One essential advantage of the embodiment of the plug connections shown is that upon replacement of the light-guide probe, the operator need only grasp the light-guide probe 21 and the plug connections 42 and 43 and thus does not come into contact with any non-sterile parts, such as, for instance, the instruments or the mounting parts 41. The light-guide probe may be developed either as a throw-away part for one-time use or as an easily sterilized part.

For measurement "in vivo," the indwelling catheter 23 is first of all introduced with the injection cannula or needle 22 into a vein or artery of the patient. Thereupon the injection needle 22 is pulled out of the catheter 23 and the measurement head 21a introduced into the catheter 23. When the plug connections 42 and 43 have been inserted in the mountings 41 the instrument is ready for measurement. A computer connected with the diode line 12b of the spectrometer 12 determines the oxygen concentration of the blood from the position of the maxima and displays it to the anesthetist. Of course, recording and/or acoustic signalling upon passage below a critical value are also possible.

What has been referred to above as the illuminating device 11 may also be called the illuminating section or portion of the apparatus, comprised of the walls or housing forming a chamber or cavity together with the illuminating parts 11a and 11b and the socket 41 mounted in or on this chamber. Likewise what has been referred to above as the spectrometer 12 may also be called the spectrometer section or portion of the apparatus, comprised of the walls or housing forming a chamber or cavity together with the parts 12a, 12b, and socket 41 mounted therein or thereon. It may be emphasized here, that because of the interfitting and precise mating construction of the light fiber plugs 42 and 43 and their respective receiving sockets 41, a correct alignment of the optical fibers is assured when the doctor or medical technician using the apparatus inserts the plugs in their respective sockets by a simple straight inserting movement, grasping the plugs alone and without having to touch any part of the illuminating portion or spectrometer portion of the apparatus, which may not necessarily be sterile, whereas the plugs and the attached probe or catheter are intended to be sterile. With the present construction, the probe or catheter may be removed from the illuminating and spectrometer portions of the apparatus, to be thrown away or to be sterilized for re-use, and a fresh sterile probe or catheter may be connected quickly and effectively without any need for the operator to come into contact with unsterilized parts of the apparatus. The probe together with the two plugs and the connecting optical fibers may be collectively referred to as the probe assembly or catheter assembly.

What is claimed is:

1. Apparatus for spectral measurement in the bloodstream, said apparatus comprising:
   (a) an illuminating section including a first plug socket and illuminating means for directing light to said first plug socket;
   (b) a spectrometer section including a second plug socket and spectrometer means responsive to light coming from said second plug socket; and
   (c) a light guide probe assembly including a probe having a measurement head, a first plug detachably inserted in said first plug socket, a second plug detachably inserted in said second plug socket, and light transmitting fibers operatively connecting said first plug and second plug to said probe;
   (d) said light transmitting fibers including a first set of light guide fibers extending from said first plug through said light guide probe to said measurement head, said first set of fibers having exposed ends in fixed position in said first socket, positioned to receive light from said illuminating means and constituting means for transmitting such light along said fibers to said measurement head;
   (e) said light transmitting fibers also including a second set of light guide fibers extending from said measurement head through said light guide probe to said second plug, said second set of fibers constituting light guide means for transmitting light from said measurement head to said second plug;

(f) said second set of light guide fibers at said second plug having exposed exit end surfaces arranged side by side along a thin straight line and positioned to constitute means forming by themselves an entrance slit for said spectrometer means without the need for a conventional slit;

(g) each of said plug sockets and its associated plug being so shaped relative to each other that each plug may be inserted in its socket by a straight longitudinal motion in only a single position of orientation;

(h) a spring-pressed pivoted latch associated with said first plug socket, said latch being displaced by insertion of said first plug into said first socket to a position in which said latch presses said first plug against one side of said first socket to hold it in definite predetermined position in said first socket, to insure that said exposed ends of said first set of fibers are in definite predetermined position relative to said illuminating means, said latch swinging to a position closing said first plug socket when said first plug is withdrawn from said first plug socket, to prevent passage of light from said illuminating means out through said first plug socket;

(i) said spectrometer means being a diode line spectrometer having an aperture ratio sufficient to receive the aperture of said exit end surfaces of said second set of light guide fibers without trimming; and (j) said measurement head of said light guide probe having a diameter of not more than 0.5 mm.

2. Apparatus as defined in claim 1, wherein said illuminating means includes a xenon lamp and a curved mirror for reflecting and concentrating rays from said lamp onto said exposed ends of said first set of fibers in said first socket.

3. Apparatus as defined in claim 1, wherein said spectrometer means includes holographic concave grating interposed in an optical path between said exit end surfaces of said second set of light guide fibers and said diode line spectrometer, said grating having an aperture angle substantially corresponding to the aperture angle of said exit end surfaces, so that said grating receives all light output from said exit end surfaces, without trimming, and substantially the entire grating is illuminated by said output.

* * * * *